(12) United States Patent
Galliher et al.

(10) Patent No.: US 10,190,087 B2
(45) Date of Patent: Jan. 29, 2019

(54) SINGLE USE CONTROLLED ENVIRONMENT MODULE

(71) Applicant: GE HEALTHCARE BIO-SCIENCES CORP., Piscataway, NJ (US)

(72) Inventors: Parrish M. Galliher, Littleton, MA (US); Michael Fisher, Ashland, MA (US); Geoffrey L. Hodge, Sutton, MA (US)

(73) Assignee: GE HEALTHCARE BIO-SCIENCES CORP., Marlborough, MA (US)

( * ) Notice: Subject to any disclaimer, the term of this patent is extended or adjusted under 35 U.S.C. 154(b) by 1486 days.

(21) Appl. No.: 13/623,584

(22) Filed: Sep. 20, 2012

(65) Prior Publication Data

US 2013/0017131 A1 Jan. 17, 2013

Related U.S. Application Data

(63) Continuation-in-part of application No. 11/050,133, filed on Feb. 3, 2005, now Pat. No. 8,298,054.
(Continued)

(51) Int. Cl.
*C12M 1/12* (2006.01)
*B01L 1/02* (2006.01)

(52) U.S. Cl.
CPC ............ *C12M 37/00* (2013.01); *B01L 1/025* (2013.01); *B01L 2300/123* (2013.01); *B01L 2400/0487* (2013.01)

(58) Field of Classification Search
CPC ... C12M 37/00; B01L 1/025; B01L 2300/123; B01L 2400/0487
(Continued)

(56) References Cited

U.S. PATENT DOCUMENTS 2,786,740 A * 3/1957 Taylor ...................... B25J 21/02
                                                              312/1
3,819,106 A * 6/1974 Schuster ............ A61B 10/0096
                                                              206/439
(Continued)

FOREIGN PATENT DOCUMENTS

CN        1119040 A     3/1996
CN        1617747 A     5/2005
(Continued)

OTHER PUBLICATIONS

PCT International Search Report dated May 13, 2014 Issued on Corresponding Patent International Application No. PCT/US2013/060827.
(Continued)

*Primary Examiner* — Helena Kosanovic
(74) *Attorney, Agent, or Firm* — Grogan, Tuccillo & Vanderleeden, LLP

(57) ABSTRACT

Disclosed herein is a single use, controlled environment manufacturing module in the form of a sterile sealed bag formed of a substantially flexible material, such that the bag can be inflated and deflated for transport and/or disposal. The flexible bag has one or more access ports and connectors to accommodate a variety of biochemical or pharmaceutical manufacturing processes to be carried out within the flexible bag. The interiors of one or more disclosed modules can be connected, forming a module train.

13 Claims, 10 Drawing Sheets

Related U.S. Application Data

(60) Provisional application No. 61/561,105, filed on Nov. 17, 2011, provisional application No. 60/541,572, filed on Feb. 3, 2004.

(58) Field of Classification Search
USPC .......................................... 454/49; 422/544
See application file for complete search history.

(56) References Cited

U.S. PATENT DOCUMENTS

| | | | |
|---|---|---|---|
| 5,576,946 A * | 11/1996 | Bender | G05B 19/41865 700/17 |
| 6,190,913 B1 | 2/2001 | Singh | |
| 6,673,598 B1 * | 1/2004 | Akers | C12M 23/14 435/297.2 |
| 7,077,486 B2 * | 7/2006 | Tattershall | B01L 1/50 312/1 |
| 2006/0179922 A1 * | 8/2006 | Sacca | G01M 3/3218 73/49.2 |
| 2008/0139865 A1 | 6/2008 | Galliher et al. | |
| 2010/0209966 A1 * | 8/2010 | Everett | C12M 21/02 435/41 |
| 2011/0058986 A1 * | 3/2011 | Yokoi | A61L 2/0094 422/111 |
| 2012/0031042 A1 | 2/2012 | Zambaux | |
| 2012/0077243 A1 | 3/2012 | Niazi | |
| 2013/0015204 A1 * | 1/2013 | Gol | B65D 1/0238 222/129 |

FOREIGN PATENT DOCUMENTS

| | | |
|---|---|---|
| CN | 1942840 A | 4/2007 |
| CN | 102066897 A | 5/2011 |

OTHER PUBLICATIONS

European Search Report Application No. 13839805.2.-1712 dated Jun. 19, 2017
CN Search Report dated Apr. 10, 2017 on Application No. 201380049172.1.
European Search Report Application No. 13839805.2.-1712 dated Oct. 5, 2017.

* cited by examiner

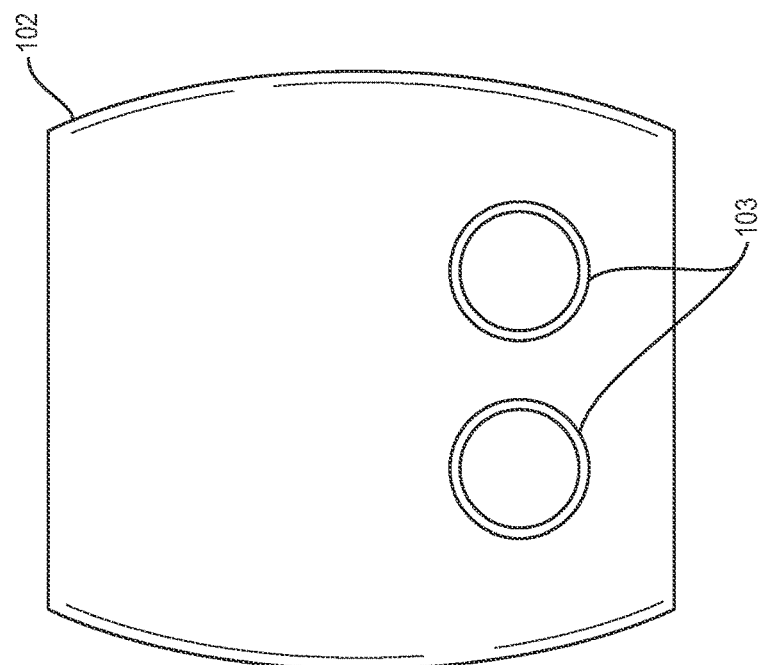
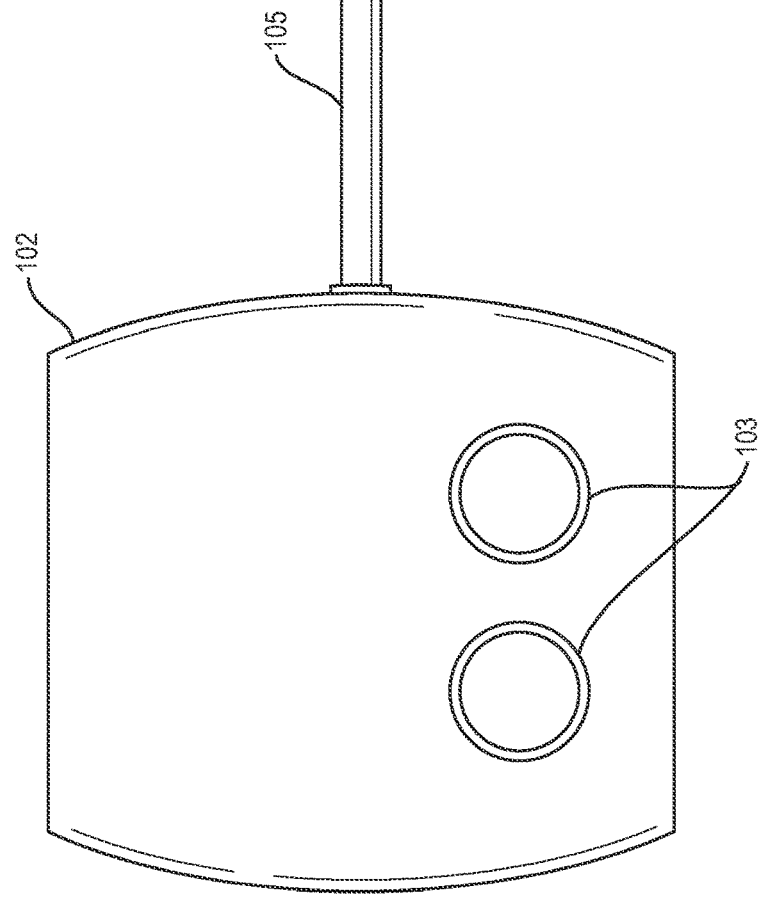
FIG. 6

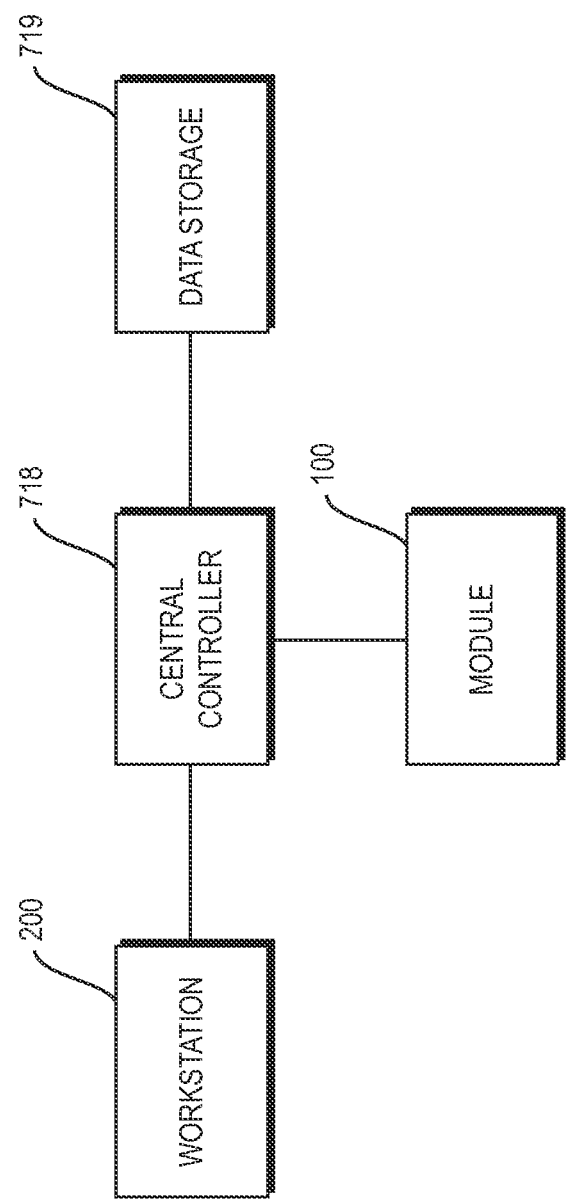

SINGLE USE CONTROLLED ENVIRONMENT MODULE

This application claims the benefit pursuant to 35 U.S.C. § 119(e)(1) of U.S. Provisional Application No. 61/561,105 filed Nov. 17, 2011. This Application is also a continuation-in-part of application Ser. No. 11/050,133 filed Feb. 3, 2005, which claims the benefit pursuant to 35 U.S.C. § 119(e)(1) of U.S. Provisional Application No. 60/541,572, filed Feb. 3, 2004. The disclosure of all of the applications listed above are hereby incorporated by reference in their entirety.

BACKGROUND OF THE INVENTION

The present invention is directed to manufacturing systems in general, and more specifically, to a flexible manufacturing platform, which includes single-use or disposable, flexible modules.

With bio/chemical/pharmaceutical manufacturing, the speed for producing drugs for clinical trials and the speed to market are important factors. Clinical milestones impact the value of the drug pipeline, stock values, financing, partnering and licensing opportunities. In addition, the high cost of drug development has been a topic of increasing interest within the industry and appears as part of the public concern regarding rising health care costs.

Much of the expense of biopharmaceutical manufacturing can be attributed to the capital investment required to build manufacturing infrastructure for producing a particular drug. Ideally, having manufacturing capacity immediately available to support every clinical and commercial need would greatly speed development of drugs. However, the capital investment required to build such bio-manufacturing capacity is too great, especially since facilities would sit idle while waiting for the drug in the development pipeline. Because development timelines, dosages, market size, clinical success, and regulatory approval are all uncertainties, the dilemma is compounded by the difficulty in accurately predicting production capacity requirements.

Due to the foregoing uncertainties and the high probability that an individual drug will fail during clinical trials, any investment in facilities for manufacturing drugs prior to successful clinical trials and/or regulatory approval is a high risk endeavor.

To reduce such expenses, an ideal manufacturing facility would be one that is inexpensive to build, can be rapidly expanded and reconfigured to handle new processes and produce drugs quickly. Moreover, it would be advantageous for such a manufacturing facility to be able to maintain and improve upon the high level of quality required for current good manufacturing practice (cGMP) for drug manufacture e.g., conformance with 21 C.F.R. Part 11).

Other manufacturing expenses may be attributable to, for example, the extensive use of non-disposable components. Such components are relatively expensive, and must be cleaned after every use. For example, stainless steel vessels are used extensively in drug manufacturing processes. Such vessels must be connected by stainless steel piping to other unit operations, media and buffer supply, water and clean-in-place and steam-in-place systems. The fabrication and installation of these vessels, and all the utilities that support them, is expensive and requires considerable lead time to design and manufacture.

Even assuming that a manufacturing facility can be built, the resulting facility is often difficult to reconfigure for new processes, or is prohibitively expensive to build in a configuration suitable for manufacturing multiple products simultaneously. Such a manufacturing scheme must be replicated in several parallel clean room environments, separated by airlocks, accessed through clean corridors, and served by dedicated HVAC units.

SUMMARY OF THE INVENTION

Non-limiting embodiments of the present invention are directed to manufacturing systems/platforms which are both flexible and efficient for manufacturing, e.g., bio-pharmaceuticals.

One embodiment of the invention is a single-use, controlled environment manufacturing module including a sealed bag formed of a substantially flexible material, the sealed bag having an interior and an exterior and capable of being inflated with air or another gas, such that an environment within the sealed bag is segregated from an ambient environment outside of the sealed bag; an external connector, the external connector comprising at least one of an aseptic connector and a tubing connector that extends from the exterior of the sealed bag to the interior of the sealed bag; and at least one set of access ports configured to provide access to the interior of the sealed bag.

Another embodiment of the invention includes a single-use, controlled environment manufacturing system comprising: a first and a second interconnected module, the first and the second interconnected modules each comprising a first and a second seated bag, respectively, formed of a substantially flexible material and having an interior and an exterior and capable of being inflated with a gas such that, when the first and the second bags are inflated with the gas, an environment within each of the first and the second bags, respectively, is segregated from an ambient environment outside of each said bag.

Also disclosed herein is a controlled environment manufacturing module comprising: a hood formed of a substantially flexible material, and a pressurized air source that focuses a flow of filtered air to an area underneath the hood such that the area underneath the hood is cleaner than ambient room air.

In another illustrative, non-limiting embodiment, a disposable module is either formed from a disposable, flexible bag cast as one entire seamless envelope, or formed by fusing or bolting several flexible panels together to produce a three-dimensional disposable chamber. If fitted with a pressurized air or other gas source, the bag is inflated and can house equipment or provide internal space for making tubing connections therein. If the pressurized gas source is fitted with a filter, then the inflated bag can provide an internal atmosphere that is cleaner than the surrounding environment.

If the air source is controlled (pressure control, gas flow rate control, etc.) then the disposable bag is provided with a controlled environment.

Yet another embodiment of the invention is a customizable, modular, clean-room type manufacturing system as an alternative to separate environmentally controlled clean rooms, the manufacturing system comprising:

a first module comprising a sealed bag formed of substantially flexible material and having a first module interior segregating a first environment of the first module interior from an ambient environment outside of the first module, and a first on-board environmental control system for controlling the first environment within the first module interior, wherein the first on-board environmental control system maintains the first environment at a positive pressure relative to the ambient environment, and is arranged for controlling a first air handling system configured for providing a first module supply air to the first environment, and for exhausting an exhaust air from the first environment; a first component disposed within the first module interior and configured to perform a first specific task chosen from a biological and a pharmaceutical manufacturing process, and a combination thereof, with the proviso that the first specific task is not that of controlling the first environment within the first module interior; a second module comprising a sealed bag formed of substantially flexible material and having a second module interior segregating a second environment within the second module interior from the ambient environment outside of the second module, and a second on-board environmental control system for controlling the second environment within the second module interior, wherein the second on-board environmental coin system maintains the second environment at a positive pressure relative to the ambient environment, and is arranged for controlling a second air handling system configured for providing a second module supply air to the second environment, and for exhausting an exhaust air from the second environment; a second component disposed within the second module interior and configured to perform a second specific task chosen from a biological and a pharmaceutical manufacturing process, and a combination thereof, with the proviso that the second specific task is not that of controlling a second environment within the second module interior, and wherein the second specific task is the same or different from the first specific task; and a central controller configured to control and monitor in real time at least one of the first and second specific tasks in at least one of the first module and the second module and to perform information collection for the operation of the system including at least one of monitoring temperatures, humidity, differential pressures, and particle counts of the modules, the customizable, clean-room type manufacturing system thereby capable of being an alternative to separate environmentally controlled clean rooms.

Rather that being cleaned or sanitized after each use, the disposable bag can be discarded after a single use. In non-limiting embodiments, less expensive materials can be used for the walls of the single-use bag because the single-use bags do not have to withstand the wear and tear of repeated re-use. Also, less labor and materials are required for cleaning (and its validation) of the disposable bag, as compared to standard clean rooms because cleaning and the cost of cleaning procedures can be avoided.

BRIEF DESCRIPTION OF THE DRAWINGS

Aspects of illustrative, non-limiting embodiments of the present invention will become more apparent by describing in detail embodiments thereof with reference to the attached drawings in which:

FIG. 6 shows two single-use, controlled environment manufacturing modules interconnected together to form a module train; and FIG. 7 is a diagram depicting a central controller unit arrangement;

DETAILED DESCRIPTION OF THE INVENTION

Figure 1:
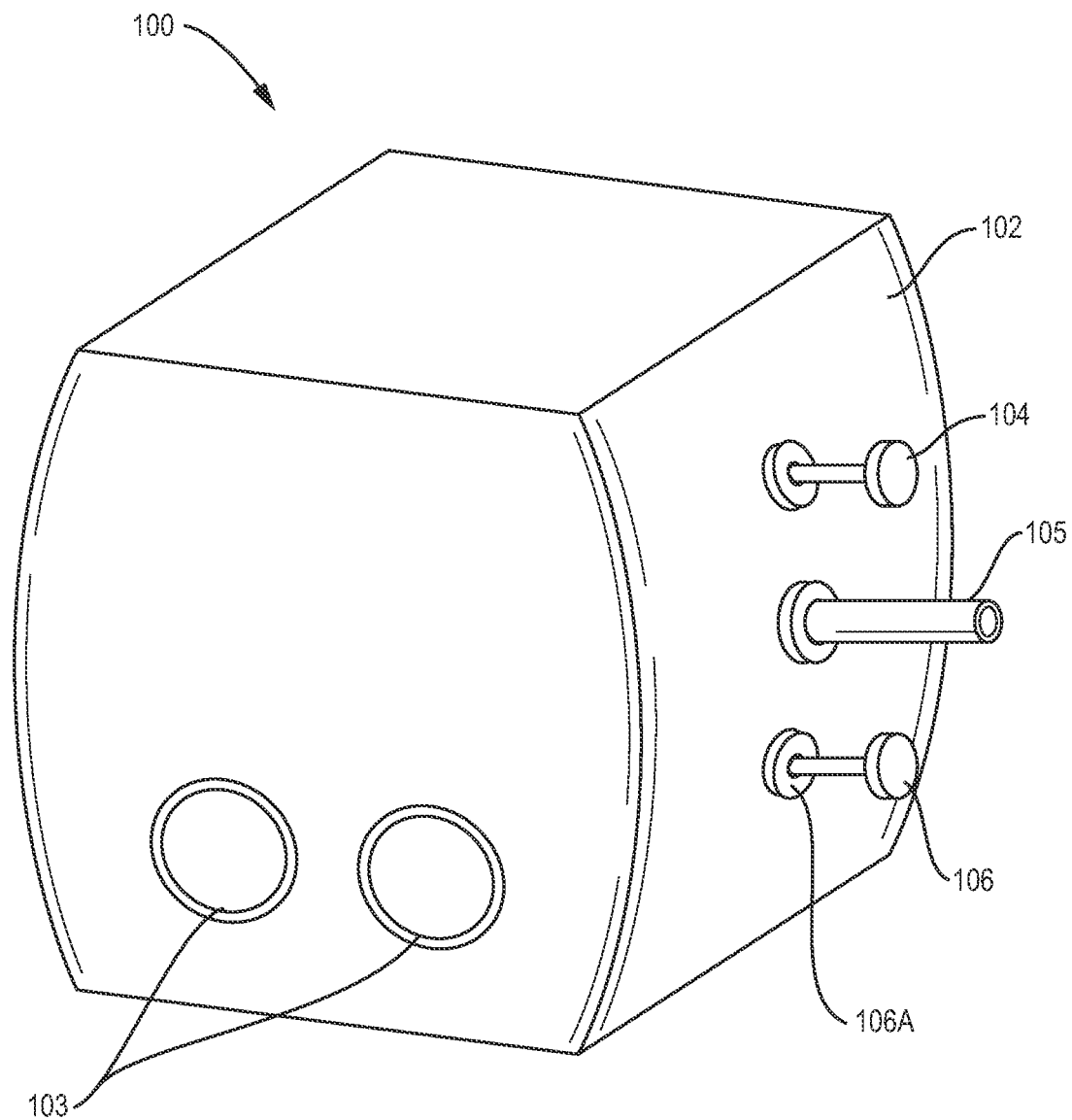
FIG. 1 shows a perspective view of a single-use, single-use, controlled environment manufacturing module.

The following description of illustrative, non-limiting embodiments of the invention discloses specific configurations and components. However, the embodiments are merely examples of the present invention, and thus, the specific features described below are merely used to more easily describe such embodiments and to provide an overall understanding of the present invention. Accordingly, one skilled in the art will readily recognize that the present invention is not limited to the specific embodiments described below. Furthermore, the descriptions of various configurations and components of the present invention that are known to one skilled in the art are omitted for the sake of clarity and brevity.

The invention allows, for example, for fixed fermentation and processing equipment used in conventional scale manufacturing suites, for example, having separate environmentally controlled clean rooms which may now be replaced with single-use or disposable modules for one or more steps of a drug or biological manufacturing process. The module operations allow for segregation from typical sources of process contamination: e.g., personnel, multi-use equipment and ambient air. In some embodiments, environmental control may be defined as controlling one or more of air flow, heat, cold, humidity and pressure. As used herein, the terms "disposable" and "single-use" have the same meaning and are used interchangeably.

The system according to some embodiments may be designed to handle multi-product, concurrent biochemical or pharmaceutical manufacturing in a common, unclassified (or classified) manufacturing space, using either a single, disposable module or a plurality of connected disposable modules (module train). The ability to use an unclassified space is due to the integrity and control of the environment inside the module for one or more steps of the manufacturing process. Such concurrent manufacturing activities may include both upstream and downstream bio-processing as well as bulk drug substance and drug product filling operations for one or more products.

Modules, according to some embodiments of the invention, may be designed and qualified to provide self-contained manufacturing environments that assure appropriate industry standard environmental quality (e.g., Class 100, Class 10,000). Modules may be connected in any order as dictated by a product's manufacturing process. Thus, according to some embodiments of the invention, the module system of bio-pharmaceutical manufacturing as well as associated control and monitoring systems, enable the system to offer additional capabilities over and above those of more traditional plants. Specifically, the system supports the rapid reconfiguration and concurrent operation of multiple manufacturing stages, e.g., from culture inoculation to bulk filling, in a common unclassified manufacturing space.

The use of a disposable module allows for a more practical and less expensive platform system by eliminating the need for clean-in-place (CIP) and sterilization-in-place (SIP) operations, thereby minimizing fluid transfer lines (e.g., steam) and corresponding required manipulations. The elimination of these required utilities is significant-modules require only power and/or data connections, and in some cases gasses, to support manufacturing operations.

Some embodiments of the invention also utilize centralized and/or remote electronic monitoring, control, automation and data record production and storage for a manufacturing batch process using a central controller (for example). Process automation may be used to reduce the number of manual operations, resulting in a reduction of operator error and an increase in the operability, efficiency and/or the reliability of the system.

Equipment for bio-processing may be contained inside each disposable module, and is typically physically and electronically integrated therein. For example, valves may be attached to a modules watt or an internal frame of the module; control panels may be separated and/or removed to the exterior of a module for ease of access. Motors and drive units may be placed outside the module for ease of access while a pump head or similar process component of the motor/pump/drive unit penetrates (preferably, sealably) into the interior of the module. Sensors for monitoring (environmentally or otherwise) may be also integrated into the body of a module and communicating with the central controller to provide continuous online monitoring of many (if not all) parameters of the operation (e.g., non-viable and viable particulates).

Other aspects of the disclosed subject matter include module portability, a factor to which the system's flexibility can be at least partially attributed. The single-use modules may be easily moved from one location to the next for qualification, setup, and operation. In addition, each single-use module may include connection ports to allow the interior of modules to be easily coupled to each other. This enables easy transfer of materials between unit operations and/or to containers to enable transfer of materials into and out of modules from the manufacturing space. Access to the interior, to access doors and ports of a module may be accomplished by the inclusion of one or more glove ports, which maintains the environment within the module.

FIG. 1 depicts a non-limiting embodiment of a single-use module 100. The single-use module 100 is formed of a flexible bag 102 cast as one entire seamless envelope that is inflated for use or created by fusing or bolting several flexible panels together to create a three-dimensional flexible chamber. The flexible bag 102 can be deflated and discarded after a single use instead of being cleaned or sanitized after each use. Because it does not have to withstand the wear and tear of repeated re-use, the flexible bag 102 or a set of flexible panels can be formed of relatively lower cost materials. Non-limiting examples of such low cost materials include polyethylene, polypropylene, polyvinylchloride, and the like. Use of a single-use module as compared to standard clean rooms results in less labor for cleaning and cleaning validation procedures. As shown in FIG. 1, an exemplary embodiment of the disposable module 100 is provided with multiple components including access ports 103, a closed aseptic connector 104, a tubing connector 105, and a sensor assembly 106. The access ports 103 may include hand or tubing access ports such as gloves, iris ports, zippers, flaps, or fully open ports. The closed aseptic connector 104 can be a single or double-ended aseptic connector that spans the wall of the flexible bag 102. The tubing connector 105 can be welded to external tubing or sealed off if no external connection is needed. Furthermore, the tubing connector 105 can connect with the flexible bag 102 via ports such as zippers, iris ports, etc., or via closed connections that are fitted, welded or bolted to the flexible bag 102. The sensor assembly 106 is inserted into a sensor port 106A on the wall of the flexible bag 102 and provides for data collection. For example, the sensor in sensor assembly 106 can measure parameters such as HVAC air flow rate, pressure, temperature, UV, pH, liquid flow, particle count, microbiology detection, humidity, etc. The sensor of sensor assembly 106 can also be connected either directly via hardwire or connected wirelessly to a computer control system or central controller in order to provide for remote monitoring of the environment within the flexible bag 102 (See also FIG. 7.). Also, the flexible bag 102 can be provided with a sealed electrical port to provide for data connection.

Figure 2:
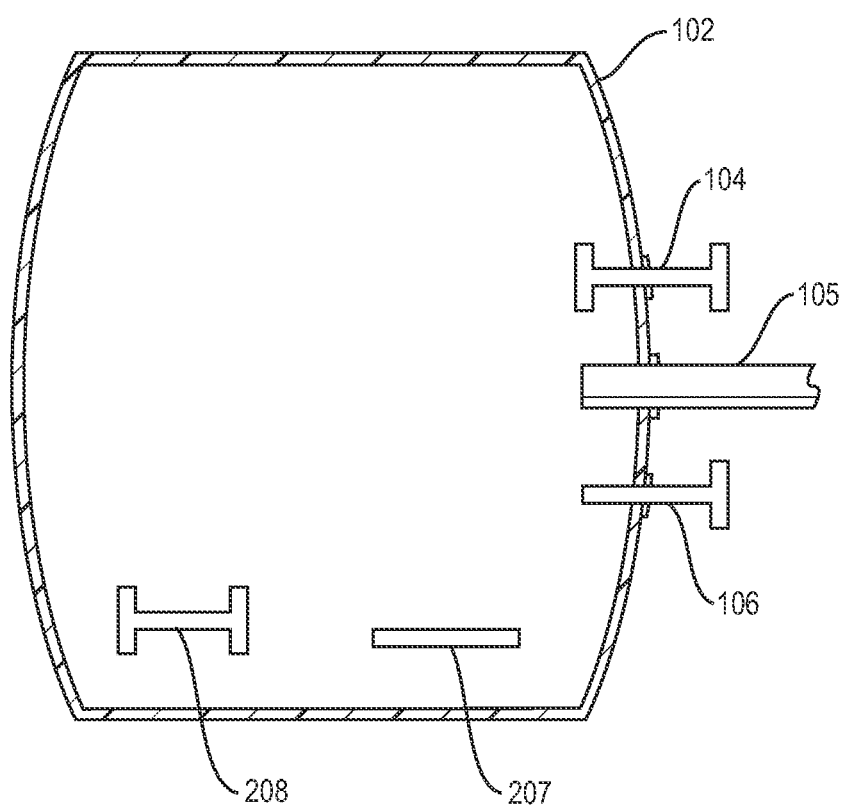
FIG. 2 is a sectional view depicting internal components of the single-use manufacturing module.

FIG. 2 is a diagram showing components that may be provided internal to the flexible bag 102. For example, the flexible bag 102 may contain a closed aseptic connector 208 (single or double ended) and a tubing connector 207 sealed entirely therein. The internal components can be used to make cross connections between various connectors or other tubing attached outside of the flexible bag 102. The flexible bag 102 can be manufactured to have any number of the components, such as pre-cut lengths of clean tubing (with or without connectors) already sealed therein such that the flexible bag can be ready for use in a variety of processes. Any components not utilized remain at the bottom of the interior of flexible bag 102 during use. The flexible bag 102 can also be manufactured for specific uses wherein each flexible bag 102 will contain a predetermined number and type of both external and internal components. Also, since the atmosphere inside the flexible bag 102 is cleaner than the outside atmosphere, the internal connections do not have to be sealed via welding, etc. It is noted that the connectors are not limited to an aseptic connector and a tubing connector, and may include any other type of suitable connector depending upon the required use.

Furthermore, pumps can be mounted inside the flexible bag 102 or split between inside and outside of the flexible bag 102 such that the drive motor portion of a pump is external to the flexible bag 102 and the pump head is internal to the flexible bag 102. The pumps may be, for example, directed drive pumps or magnetic drive pumps. Similarly, bubble traps (re-useable or single-use) can be mounted entirely within the flexible bag 102 or split to be mounted both inside and outside of the flexible bag 102. In the case of a split bubble trap, the bubble trap vessel is provided inside the flexible bag 102 and the vent system is provided outside the flexible bag 102.

Non-limiting embodiments of the single-use module 100 are not required to contain each component discussed above and may contain a plurality of each component and/or any combination of one or more of the components.

Figure 3:
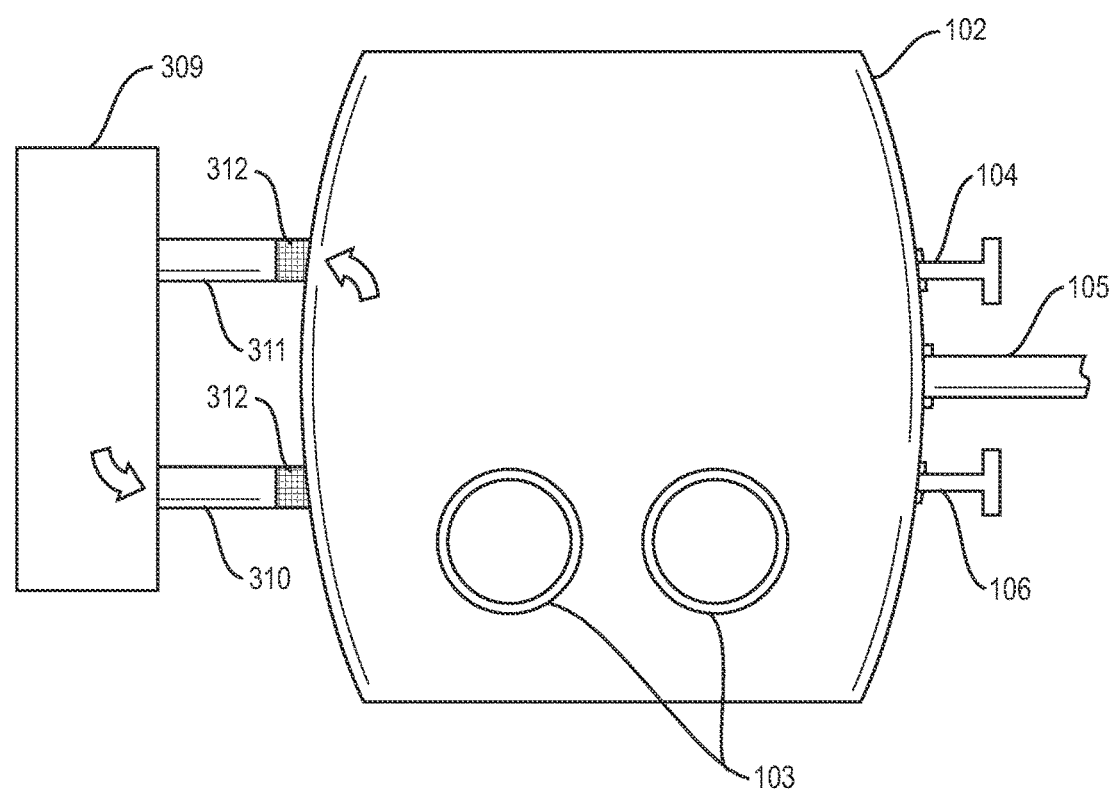
FIG. 3 is a front view of the single-use manufacturing module connected to a pressurized air source or computer controlled HVAC system.

FIG. 3 depicts the flexible bag 102 fitted with an air handling system 309 that functions as an environmental control system. The air/gas handling system 309 as shown is provided with an air/gas supply tube 310 and an air/gas exhaust tube 311. The gas supply tube 310 and the gas exhaust tube 311 can both be provided with filters 312, such as HEPA filters, in order to filter the air or gas entering and exiting the flexible bag 102. Also, the flexible bag 102 can be provided with a pressurized air source that supplies filtered air or gas therein. The pressurized air source would be analogous to the air handling system 309 except that no air/gas exhaust tube 311 would be provided. If the pressurized air source is provided with a filter 312, the flexible bag 102 would essentially contain an internal atmosphere that is cleaner than the surrounding environment. The filter 312 can be fixed to the wall of the flexible bag 102 or the flexible bag 102 can be fitted with a ferrule to which external filters are attached. Also, the temperature and humidity of the air/gas supplied to the single-use module 100 can be controlled. A damper control on the intake or exhaust may be used to regulate module pressurization for positive pressure within the module during processing.

The air handling system 309 can be made detachable via the tubes 310 and 311, such that the flexible bag 102 can be transported in a flattened or collapsed state. The air handling system 309 can later be attached to the tithes 310 and 311 to inflate the flexible bag 102 for use. Similarly, the pressurized air source can be made detachable. In another non-limiting embodiment, the flexible bag 102 may be manufactured in an already inflated state such that no air handling system or pressurized air source is necessary. Furthermore, the air handling system 309 or pressurized air source can be used in combination with any of the non-limiting embodiments discussed herein and is not limited to the embodiment shown in FIG. 3.

When the sensor within sensor assembly 106 and/or other sensors are connected to the air handling system 309 (either wirelessly or directly) or to another pressurized air source, the flexible bag 102 is provided with a controlled environment with regard to pressure, gas/air flow rate, etc.

A single-use controlled environment manufacturing module can be ventilated to provide and maintain a cleaner air than or segregated environment from its surroundings, and the amount or rate of ventilation can be controlled. For example, the manufacturing module can be ventilated with recirculated air/gas or with a single pass once through, of air/gas flow with or without filtration. A single-use manufacturing module according to the invention can be ventilated by means of a single pass of filtered air; or compressed air/gas via a vent port fitted with or without filtration. In another embodiment, the disclosed manufacturing module is totally sealed, and the enclosed has no air/gas supply.

In one embodiment, an on-board automatic control system can be used to control the air flow/pressure inside the single-use controlled environment module. The single use bag within the module can be fitted with gas filters that are fixed to the bag wall. Alternatively, the bag can be fitted with ferrules to which external gas filters are attached. Gas filters can be heated in order to reduce clogging of the filters by condensation.

Figure 4:
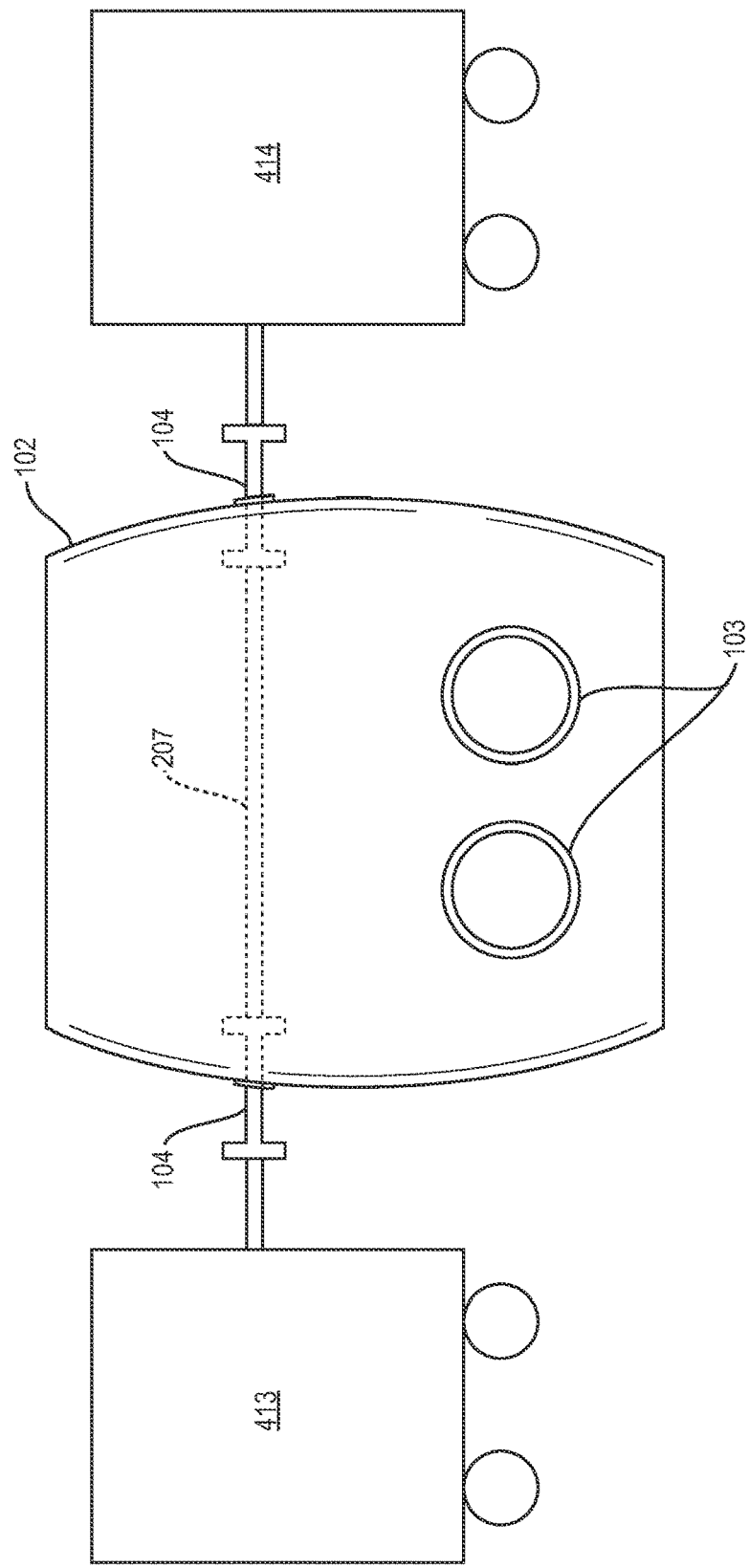
FIG. 4 shows a single-use, controlled environment manufacturing module connected between external process machinery.

FIG. 4 depicts use of the flexible bag 102 as a type of transfer panel bag. In particular, the external process machinery 113 (e.g., bioreactors, filtration system, packaging system, etc.) is connected to the external process machinery 114 via the double-ended, closed aseptic connectors 104, wherein the double-ended, closed aseptic connectors 104 connect to one another via the tubing connector 207 previously sealed within the flexible bag 102. The connection can be made manually by a user via the access ports 103. Although only one cross connection is shown, any number of cross connections can be formed by manufacturing the flexible bag 102 with additional aseptic connectors 104 and/or tubing connectors 107. Also, the transfer concept can be accomplished without any internal tubing connectors 107. In particular, materials can be transferred manually between each of die external process machinery 413, 414. Furthermore, both the external and internal connections can be made with either the aseptic connectors 104, 208 or the tubing connectors 105, 207, and are not limited to the example as shown. All connection components can be sized according to the required use (i.e., to transfer containers or components in and out of the module 100).

Figure 5:
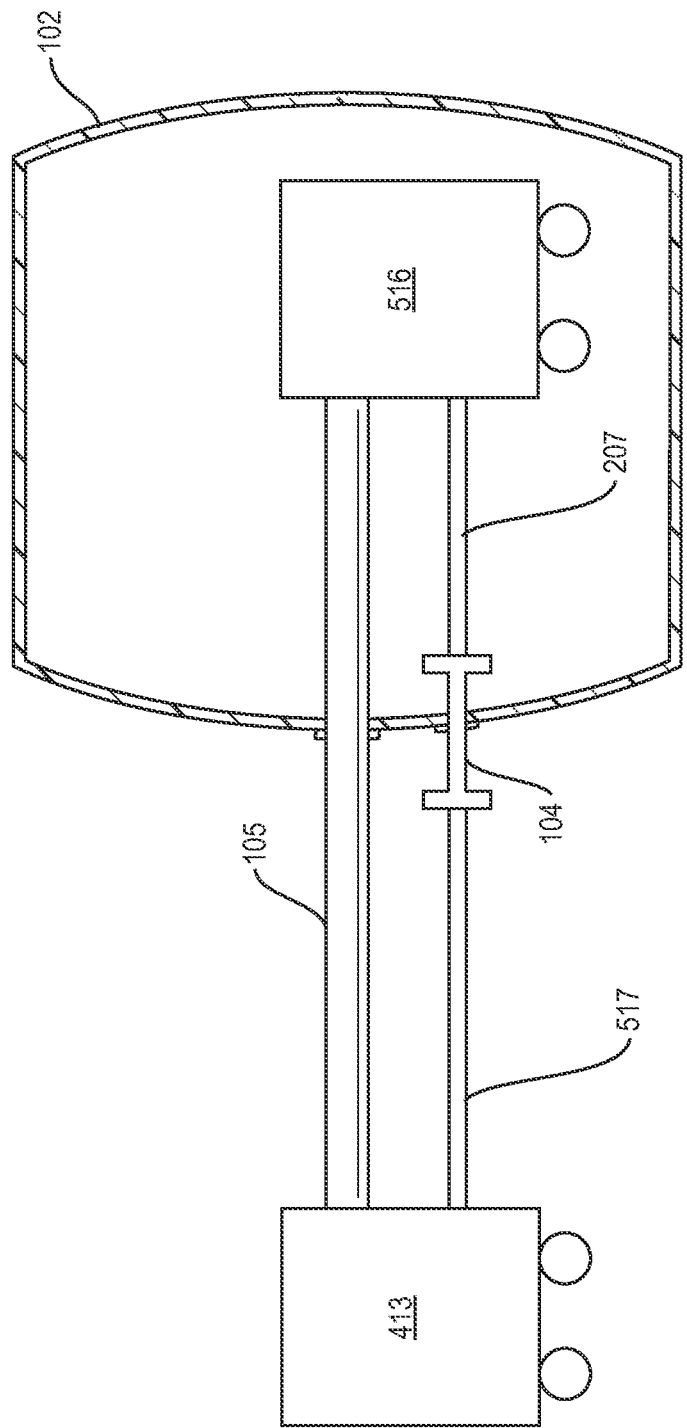
FIG. 5 shows a single-use, controlled environment manufacturing module having internal process machinery that is connected to external process machinery.

FIG. 5 depicts the use of the flexible bag 102 to connect the internal process machinery 516 (e.g., bioreactors, filtration system, packaging system, etc.) with the external process machinery 413. The external process machinery 413 is connected to the internal process machinery 516 via the tubing connector 105 as well as via the aseptic connector 104 (in combination with the external tubing connector 517 and the internal tubing connector 207). Although two types of interconnections are shown, any variation or combination of component connections can be provided. Furthermore, FIG. 6 depicts two flexible bags 102 connected to one another via a tubing connector 105. The tubing connector 105 can be sized according to the required use (i.e., to transfer containers or components between modules). The flexible bags 102 can also be connected via aseptic connectors, ports (including a flexible port and a stationary port that are clamped to one another). Any other type of connection can be used and also additional flexible bags can be provided to form a module chain where materials can be transferred from one flexible bag 102 to the next.

The single-use module 100 may also be provided with an on-board process control system used to control the processing operations inside or associated with the single-use module 100. The on-board process control system may include a central controller unit 18 (e.g., computer system, associated software and user interface) as shown in FIG. 7. The central controller unit 18 may thus be used for setup of a single module or a module train (i.e., manufacturing process) and allow for verification of correct installation of process components, monitoring, automation, process control and generation of electronic batch records for one or more individual modules or for an entire module train. For example, the status of a particular module can be readily discerned and tracked (e.g., clean, dirty, in process, assigned to a specific process, etc.) and the flow of process intermediates and materials into, between and out of modules and/or areas of a manufacturing facility may also be monitored. As shown in FIG. 7, the central controller unit or central controller 718 is connected to the single-use module 100, either via hardwire or wirelessly. The central controller unit 718 may include a data storage 719 to store data as well as applications and/or operation software, as well as a graphical-user-interface (GUI) displayable on a workstation 200. The GUI 200 may display a number of different screens for setting up, monitoring and controlling the modules and the overall manufacturing process.

Figure 8A:
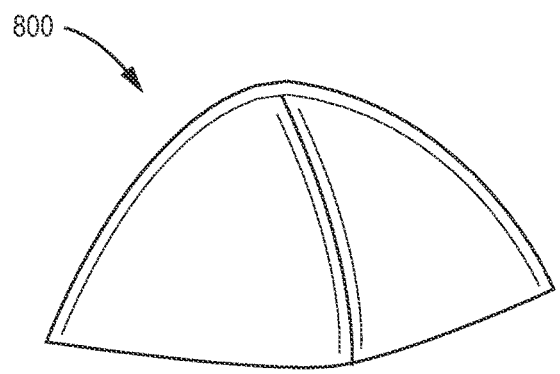
FIGS. 8A-8D shows alternate, non-limiting shapes of the single-use module.
Figure 8B:
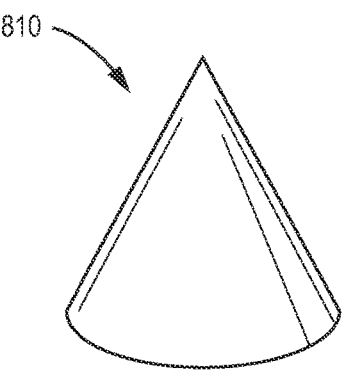
Figure 8C:
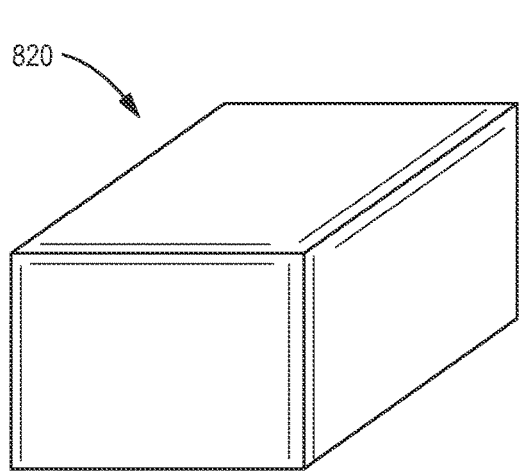
Figure 8D:
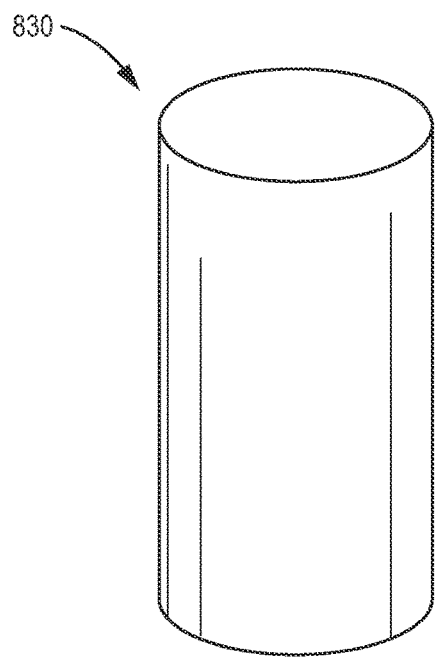

FIGS. 8A-8D show examples of alternate, exemplary shapes of the flexible bag 102 according to an embodiment of the invention. Of course, the shape of the flexible bag 102 is not limited to the shapes shown in the Figures, but may be of any other suitable shape depending upon its use. FIG. 8A illustrates a module 800 comprising at least 4 panels flexible material welded or otherwise joined together to form an enclosed module. FIG. 8B depicts a conical shaped, enclosed module 810. FIG. 8C depicts a rectangular box-shaped module 820 manufactured from several panels of flexible or semi-rigid material. FIG. 8D depicts a cylindrical-shaped module 830.

Figure 9:
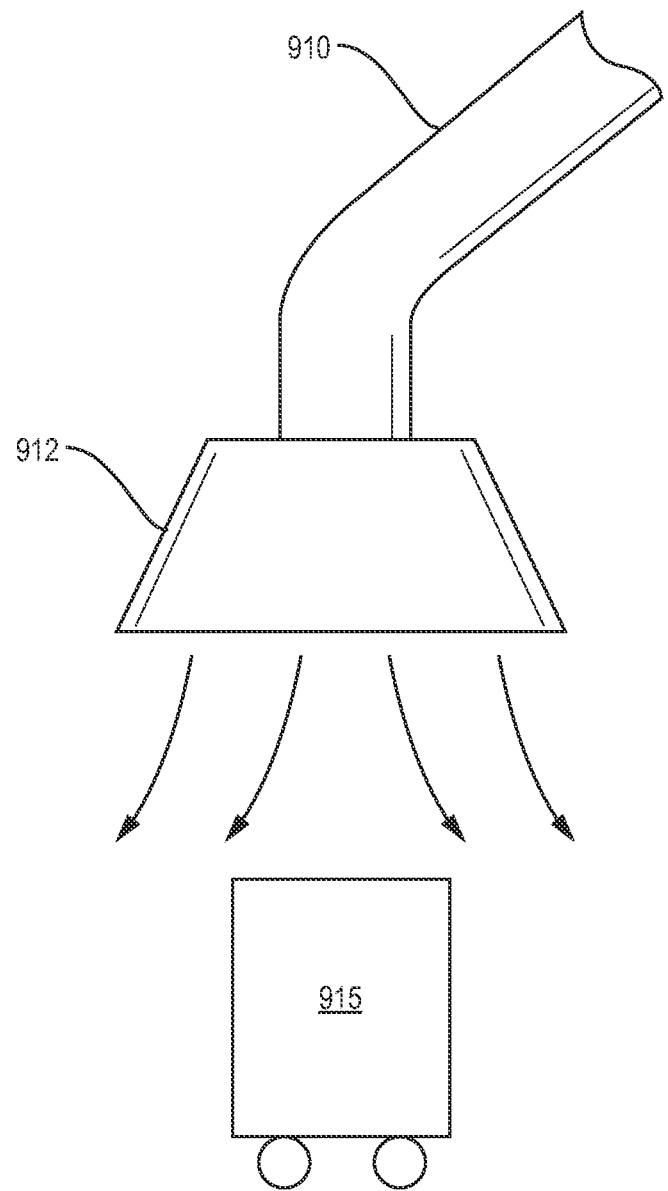
FIG. 9 shows an alternate embodiment where the single-use module is provided as a hood or umbrella.

FIG. 9 depicts an alternate embodiment in which the disposable module 921 is formed as a type of hood or umbrella formed of a flexible or a semi-rigid material, the hood-shaped module 921 connected to a filtered air supply 910 that is directed downward and focused to flow down over external process machinery 915. The air flow can be HEPA-filtered and surrounds the equipment 915 with a cleaner environment than would otherwise surround the equipment 915 in ambient room air. The module 921 can be hard-walled or flexible and disposable. In use, the air flow comprises filtered air flowing downward around process machinery 915, the filtered air being at a higher pressure than the pressure of ambient air.

Figure 10:
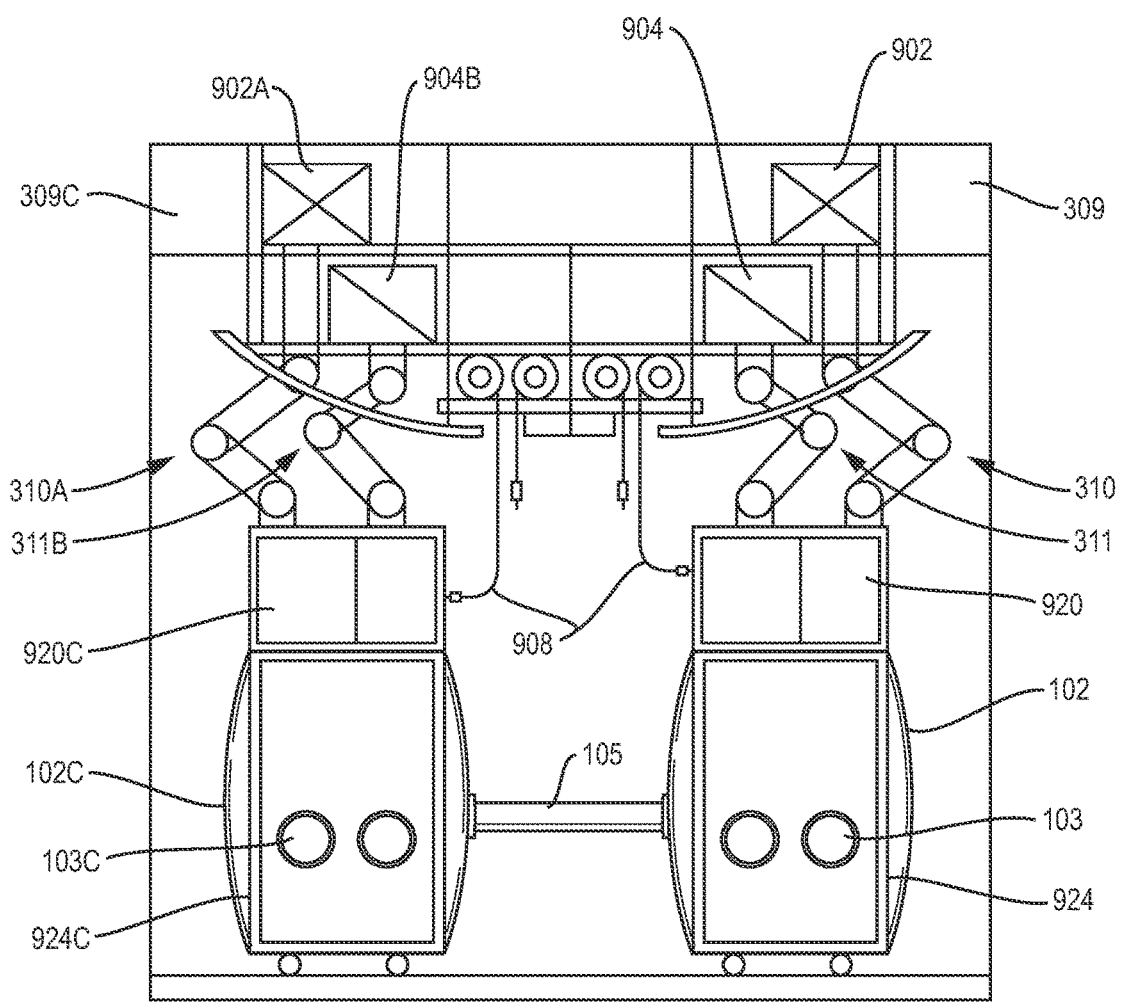
FIG. 10 illustrates a side view of a manufacturing space illustrating support utilities and connection of a module comprising a flexible bag within a rigid support structure to air supply and exhaust headers.

FIG. 10 shows a side view of a manufacturing space including support utilities and connection of a module comprising a flexible bag 102, 102C within a rigid support structure 924, 924 C to fresh air supply headers 902, 902A and exhaust gas headers, also termed "ventilation systems" 904, 904 B. The rigid support structures 924, 924C can be made of any suitable material, such as, for example, aluminum, stainless steel, or a substantially rigid polymer or plastic and can have any shape suitable for supporting the flexible bag 102, 102 C. In one embodiment, a plexi-glass panel with openings for accessing the access ports 103, 103C, is attached to the front of the support structure 924, 924 C. The air handling system 309, 309C, also referred to herein as an "HVAC system," typically comprises at least one of a heating, ventilation, air or gas supply, and air conditioning system, and is fluidically communicating with and operationally connected to its respective single-use controlled environment module 102, 102C. As described previously, one embodiment of the disclosed single-use controlled environment module is a module formed of a flexible or a semi-rigid material. As such, the single-use controlled environment modules depicted in FIG. 10 are the flexible bags 102, 102C, that are fluidically connected to one another, either continuously or intermittently, by tubing connector 105. The HVAC system 309, 309C according to one embodiment of the invention is located in the same room as the controlled environment module to which it is connected; in another embodiment the HVAC system is in a different room.

As described below, the module specific air-handling system 309, 309C generally includes drop-down HVAC snorkels, one 310, 310A for supplying fresh air 902, 902A, and one 311, 311B for collecting exhaust air from the modules 102, 102C and delivering the exhaust gas to the ventilation system 904, 904B. Such snorkels 310, 310A may be fully flexible, so as to enable easier connection to each respective module without restricting choice of a location for each module in the manufacturing space. As also shown, electrical and/or data connections 908 may be made to the on-board environmental control system 920, 920C, or can be made directly to its respective module. The air or other gas supplied to the modules may be delivered through the air handling system 309, 309 C that controls temperature (typically from about 15 to about 30.degrees Celsius) and relative humidity (typically from about (10 percent to about 60 percent relative humidity). The air is delivered via the flexible snorkel 310, 310A to a module intake blower, where it may be pre-filtered and even HEPA filtered prior to entry into the flexible bag 102, 102C of which the module is comprised.

The on-board environmental control system 920, 920C can include, for example, a HEPA filter, a control box, fans, pressure sensors, microprocessors, and particle counters. It is worth noting that, typically, the system maintains pressure within two interconnected modules such that the more downstream module preferably has a higher pressure.

FIG. 10 also depicts access ports 103, 103c that may include hand or tubing access ports such as gloves, iris ports, zippers, flaps, or fully open ports.

FIG. 10 depicts a customizable, modular, clean-room type manufacturing system as an alternative to separate environmentally controlled clean rooms, the manufacturing system comprising: a first module comprising a sealed bag 102, formed of substantially flexible material and having a first module interior segregating a first environment of the first module interior from an ambient environment outside of the first module, and a first on-board environmental control system 920, 920C for controlling the first environment within the first module interior, wherein the first on-board environmental control system 920, maintains the first environmental positive pressure relative to the ambient environment, and is arranged for controlling a first air handling system 309, configured for providing a first module supply air 902, through tube 310, to the first environment, and for exhausting an exhaust air from the first environment through exhaust tube 311, to a ventilation system 904; a first component (516 for example, as shown in FIG. 5) disposed within the first module interior and configured to perform a first specific task chosen from a biological and a pharmaceutical manufacturing process, and a combination thereof, with the proviso that the first specific task is not that of controlling the first environment within the first module interior; a second module comprising a sealed bag 102C formed of substantially flexible material and having a second module interior segregating a second environment within the second module interior from the ambient environment outside of the second module; and a second on-board environmental control system 920C for controlling the second environment within the second module interior, wherein the second on-board environmental control system 920C maintains the second environment at a positive pressure relative to the ambient environment, and is arranged for controlling a second air handling system 309C configured for providing a second module supply air 902A through tube 310 A to the second environment, and for exhausting an exhaust air from the second environment through exhaust tube 311 B to a ventilation system 904 B; a second component (not shown) disposed within the second module interior and configured to perform a second specific task chosen from a biological and a pharmaceutical manufacturing process, and a combination thereof, with the proviso that the second specific task is not that of controlling a second environment within the second module interior, and wherein the second specific task is the same or different from the first specific task; and a central controller (not shown) configured to control and monitor in real time at least one of the first and second specific tasks in at least one of the first module and the second module and to perform information collection for the operation of the system including monitoring temperatures, humidity, differential pressures, and particle counts of the modules, the customizable, clean-room type manufacturing system thereby capable of being an alternative to separate environmentally controlled clean rooms.

Non-limiting examples of equipment that can be included in a single-use controlled environment module can include disposable bioreactor bags, mixing bags, process vessels, pumps, chromatography columns or skids, filtration equipment, vial-filling equipment.

The previous description of the non-limiting embodiments is provided to enable one skilled in the art to make and use the present invention. Moreover, various modifications to these embodiments will be readily apparent to those skilled in the art, and the generic principles and specific examples defined herein may be applied to other embodiments without the use of inventive faculty. Therefore, the present invention is not intended to be limited to the embodiments described herein, but is to be accorded the widest possible scope as defined by the recitations of the claims and equivalents thereof.

What is claimed is:

1. A single use, controlled environment manufacturing module comprising:
   a sealed bag formed of a substantially flexible material, the sealed bag having sterile interior and an exterior and capable of being inflated with air or gas, such that an environment within the sealed bag is sterile and is segregated from an ambient environment outside of the sealed bag;
   at least one external connector, the at least one external connector comprising at least one of an aseptic connector and a tubing connector that extend from the exterior of the sealed bag to the interior of the sealed bag;
   at least one set of access ports configured to provide hand-access to the interior of the sealed bag; and
   a central controller operative to control and monitor the environment within the sealed bag and a manufacturing process conducted within the sealed bag;
   wherein a sterile environment is achieved and maintained within the bag without clean-in-place or sterilization-in-place operations.

2. The single use, controlled environment manufacturing module of claim 1, wherein the aseptic connector is single-ended or double-ended.

3. The single use, controlled environment manufacturing module of claim 1, further comprising at least one sensor to monitor the environment within the sealed bag.

4. The manufacturing module of claim 1, further comprising at least one internal connector contained entirely within the sealed bag and not attached to the sealed bag such that the at least one internal connector does not penetrate the sealed bag, the internal connector comprising one of an aseptic connector and a tubing connector; and
   wherein the at least one internal connector remains at a bottom of the sealed bag when not in use.

5. The single use, controlled environment manufacturing module of claim 1, further comprising an air handling system configured to control the environment within the sealed bag.

6. The single use, controlled environment manufacturing module of claim 5, wherein the air handling system is provided with an air inlet tube and an exhaust tube.

7. The single use, controlled environment manufacturing module of claim 6, wherein the air inlet tube and the exhaust tube are provided with filters to filter the air or gas entering and exiting the sealed bag.

8. The single use, controlled environment manufacturing module of claim 5, wherein the air handling system controls the temperature and humidity of the air or gas supplied to the sealed bag.

9. The single use, controlled environment manufacturing module of claim 1, further comprising a pressurized air source that supplies the air or gas into the sealed bag.

10. The single use, controlled environment manufacturing module of claim 9, wherein the pressurized air source supplies filtered air or gas into the sealed bag.

11. The single use, controlled environment manufacturing module of claim 1, wherein the environment within the sealed bag is maintained at a positive pressure relative to the ambient environment outside of the sealed bag.

12. The single use, controlled environment manufacturing module of claim 1, further comprising a first component disposed within the interior of the sealed bag and configured to perform a first specific task chosen from a group of biological and a pharmaceutical manufacturing processes, and a combination thereof.

13. The single use, controlled environment manufacturing module of claim 1, wherein the at least one external connector provides the only means of ingress into or egress out of the sealed bag such that the sterile environment is achieved and maintained within the bag without the clean-in-place or sterilization-in-place operations.

* * * * *